(12) United States Patent
Iijima et al.

(10) Patent No.: US 9,611,438 B2
(45) Date of Patent: Apr. 4, 2017

(54) METHOD AND SYSTEM FOR PRODUCING LIQUID FUEL AND GENERATING POWER

(71) Applicant: MITSUBISHI HEAVY INDUSTRIES, LTD., Tokyo (JP)

(72) Inventors: Masaki Iijima, Tokyo (JP); Ryuji Yoshiyama, Tokyo (JP); Haruaki Hirayama, Tokyo (JP); Yoshio Seiki, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/428,461

(22) PCT Filed: Sep. 4, 2013

(86) PCT No.: PCT/JP2013/073810
§ 371 (c)(1),
(2) Date: Mar. 16, 2015

(87) PCT Pub. No.: WO2014/045871
PCT Pub. Date: Mar. 27, 2014

(65) Prior Publication Data
US 2015/0232773 A1  Aug. 20, 2015

(30) Foreign Application Priority Data
Sep. 21, 2012  (JP) .................................. 2012-208105

(51) Int. Cl.
| C10L 1/08 | (2006.01) |
| C07C 29/152 | (2006.01) |
| C10G 3/00 | (2006.01) |
| C10L 1/06 | (2006.01) |
| B01J 19/24 | (2006.01) |
| C07C 41/09 | (2006.01) |
| C01B 3/38 | (2006.01) |

(52) U.S. Cl.
CPC ............... *C10L 1/08* (2013.01); *B01J 19/245* (2013.01); *C01B 3/384* (2013.01); *C07C 29/152* (2013.01); *C07C 41/09* (2013.01); *C10G 3/42* (2013.01); *C10L 1/06* (2013.01); *B01J 2219/24* (2013.01); *C01B 2203/0233* (2013.01); *C01B 2203/061* (2013.01); *C01B 2203/0811* (2013.01); *C10L 2200/0492* (2013.01); *C10L 2270/023* (2013.01); *C10L 2270/026* (2013.01); *C10L 2290/42* (2013.01)

(58) Field of Classification Search
None
See application file for complete search history.

(56) References Cited

U.S. PATENT DOCUMENTS

| 4,263,141 A | 4/1981 | Moller et al. | |
| 2009/0084035 A1* | 4/2009 | Wei ......................... | B01J 8/009 48/73 |

FOREIGN PATENT DOCUMENTS

| EA | 005783 B1 | 6/2005 |
| EA | 005958 B1 | 8/2005 |
| JP | 62-41276 B2 | 9/1987 |
| JP | 1-47515 B2 | 10/1989 |
| JP | 8-312310 A | 11/1996 |
| JP | 10-26330 A | 1/1998 |
| JP | 11-257093 A | 9/1999 |
| JP | 11-257094 A | 9/1999 |
| JP | 2000-54852 A | 2/2000 |
| JP | 2008-163873 A | 7/2008 |
| JP | 2009-85210 A | 4/2009 |
| JP | 2010-127155 A | 6/2010 |
| RU | 2 258 029 C2 | 8/2005 |
| RU | 2361900 C2 | 7/2009 |

OTHER PUBLICATIONS

Machine translation for JP H08312310,pp. 1-16.*
Concise explanation of relevance of JP 1-47515 B2 previously filed on Mar. 16, 2015.
International Search Report dated Oct. 8, 2013 issued in corresponding application No. PCT/JP2013/073810.
Notification of Transmittal of Translation of the International Preliminary Report on Patentability (Chapter I or Chapter II) (Form PCT/IB/338) of International Application No. PCT/JP2013/073810 mailed Apr. 2, 2015 with forms PCT/IB/337 and PCT/ISA/237. (7 pages).
Notice of Acceptance dated Aug. 18, 2016, issued in counterpart Australian Patent Application No. 2013319303. (3 pages).
Notice of Allowance dated Jul. 15, 2016, issued in counterpart Russian Patent Application No. 2015109699. (8 pages). (Concise statement of relevance: The date of grant was Jul. 15, 2016, and all cited references have already been made of record.).
Office Action dated Aug. 2, 2016, issued in counterpart Japanese Patent Application No. 2012-208105, with English translation. (6 pages).
Extended (Supplementary) European Search Report (EESR) dated Mar. 23, 2016, issued in counterpart European Patent Application No. 13838253.6. (6 pages).

(Continued)

*Primary Examiner* — Yong Chu
*Assistant Examiner* — Ana Z Muresan
(74) *Attorney, Agent, or Firm* — Westerman, Hattori, Daniels & Adrian, LLP

(57) ABSTRACT

A steam reformer generates reformed gas by a steam-reforming reaction of hydrocarbon gas such as natural gas. A methanol synthesis column and a gasoline synthesis column synthesize gasoline from the reformed gas via methanol and produce a liquid fuel. A superheater superheats a part of low-pressure steam that has been heat-recovered from the reformed gas with a part of middle-pressure steam that has been heat-recovered by the methanol synthesis column or the gasoline synthesis column, and the steam thereby brought into an unsaturated state is supplied to a low-pressure steam turbine.

3 Claims, 2 Drawing Sheets

(56) References Cited

OTHER PUBLICATIONS

Office Action dated Mar. 18, 2016, issued in counterpart Russian Patent Application No. 2015109699, with English translation. (11 pages).

Notice of Allowance dated Nov. 15, 2016, issued in counterpart Canadian Application No. 2,884,175. (1 page).

Notice of Allowance dated Nov. 8, 2016, issued in counterpart Japanese Patent Application No. 2012-208105, with English translation. (6 pages).

* cited by examiner

METHOD AND SYSTEM FOR PRODUCING LIQUID FUEL AND GENERATING POWER

TECHNICAL FIELD

The present invention relates to a method and a system for producing a liquid fuel such as gasoline from hydrocarbon gas such as natural gas, and for generating power.

BACKGROUND ART

As a method for producing gasoline from natural gas, JP 62-041276 B discloses a method in which synthetic gas is generated by steam-reforming natural gas, methanol is synthesized from the synthetic gas, and further, gasoline is synthesized from the methanol. In a reaction for synthesizing gasoline from methanol, a large amount of water is generated in addition to gasoline, but no method for using the generated water has been formerly studied yet.

On the other hand, JP 2000-054852 A discusses a combined cycle power generation method which uses a gas turbine, in which a steam-reforming system is coupled to a combustor of the gas turbine.

BACKGROUND LITERATURE

Patent Literature

Patent Literature 1: JP 62-041276 B
Patent Literature 2: JP 2000-054852 A

DISCLOSURE OF INVENTION

Problem to be Solved by Invention

A steam-reforming reaction is run at a very high temperature as high as about 800° C. or higher. In carrying out such a steam-reforming reaction, in order to suppress precipitation of carbon on a catalyst, it is necessary to supply steam in an amount greater than that of hydrocarbon gas, i.e., the feedstock. Accordingly, since excessive steam is included in reformed gas obtained by steam reforming, the reformed gas is condensed when it is cooled, and as a result, a large amount of heat is generated. However, because the temperature of most of the heat is as low as about 180° C. or lower, this heat does not contain any heat that is suitable for use as recycled.

In consideration of the above-described problem, an object of the present invention is to provide a method and a system for producing a liquid fuel from reformed gas generated by a steam-reforming reaction and efficiently generating power by effectively using low temperature waste heat generated by the steam-reforming reaction.

Means for Solving the Problem

In order to achieve the above-described object, according to an aspect of the present invention, there is provided a method for producing a liquid fuel from hydrocarbon gas and for generating power, the method including the steps of: reforming hydrocarbon gas to generate reformed gas by a steam-reforming reaction of the hydrocarbon gas; synthesizing gasoline, dimethyl ether, or a diesel fuel from the reformed gas via methanol; recovering heat from thermal energy of the reformed gas to obtain saturated steam having a temperature of at most 180° C. before using the reformed gas for the synthesis step; superheating the saturated steam by using a heat source having a temperature of at least 200° C. generated by the method to obtain superheated steam; and generating power by using the superheated steam.

Steam generated by an exothermic reaction in the synthesis step may be used as the heat source for the superheating in the superheating step. All of a methanol synthesis reaction, a gasoline synthesis reaction, a dimethyl ether (DME) synthesis reaction, and a diesel fuel synthesis reaction such as a Fischer-Tropsch process are exothermic reactions. Heat of these reactions alone or in combination with one another can be used to generate steam for heat recovery.

A part of the reformed gas obtained in the reforming step may be used as the heat source for the superheating in the superheating step. Alternatively, flue gas generated in the reforming step may be used as the heat source for the superheating in the superheating step.

According to another aspect of the present invention, there is provided a system for producing a liquid fuel from hydrocarbon gas and for generating power, the system including: a steam-reforming device for generating reformed gas by a steam-reforming reaction of hydrocarbon gas; a synthesis column for synthesizing gasoline, dimethyl ether, or a diesel fuel from the reformed gas via methanol; a heat exchanging device for obtaining saturated steam having a temperature of at most 180° C. by heat exchanging of the reformed gas before the reformed gas is introduced in the synthesis column; a superheating device for superheating the saturated steam by using a heat source having a temperature of at least 200° C. generated within the system to obtain superheated steam; and a power generation device for generating power by using the superheated steam.

The heat source used in the superheating device may be steam generated by an exothermic reaction in the synthesis column. Alternatively, the heat source used in the superheating device may be a part of the reformed gas obtained by the steam-reforming device. Further alternatively, the heat source used in the superheating device is flue gas generated by the steam-reforming device.

Advantageous Effects of Invention

As described above, according to the present invention, by generating superheated steam by superheating saturated steam with a temperature as low as 180° C. or lower, the wet region can be reduced if the pressure of the steam is lowered by a steam turbine, and thereby a high specific enthalpy of the steam can be obtained and the output of power generation that uses the steam can be greatly improved. Accordingly, by effectively using low-temperature waste heat as low as 180° C. or lower generated by a steam-reforming reaction, power can be efficiently generated and a method and a system for producing a liquid fuel from the reformed gas generated by the steam-reforming reaction can be provided.

DESCRIPTION OF EMBODIMENTS

Figure 1:
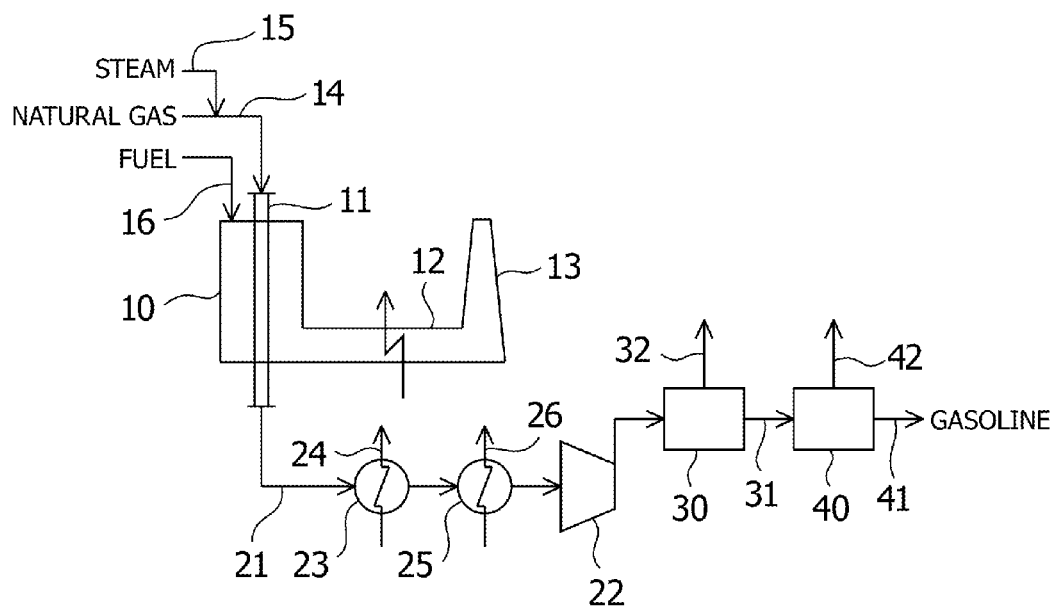
FIG. 1 is a schematic diagram showing an embodiment of a system for producing gasoline and generating power according to the present invention, which illustrates a flow of a process of producing gasoline from a feedstock.
Figure 2:
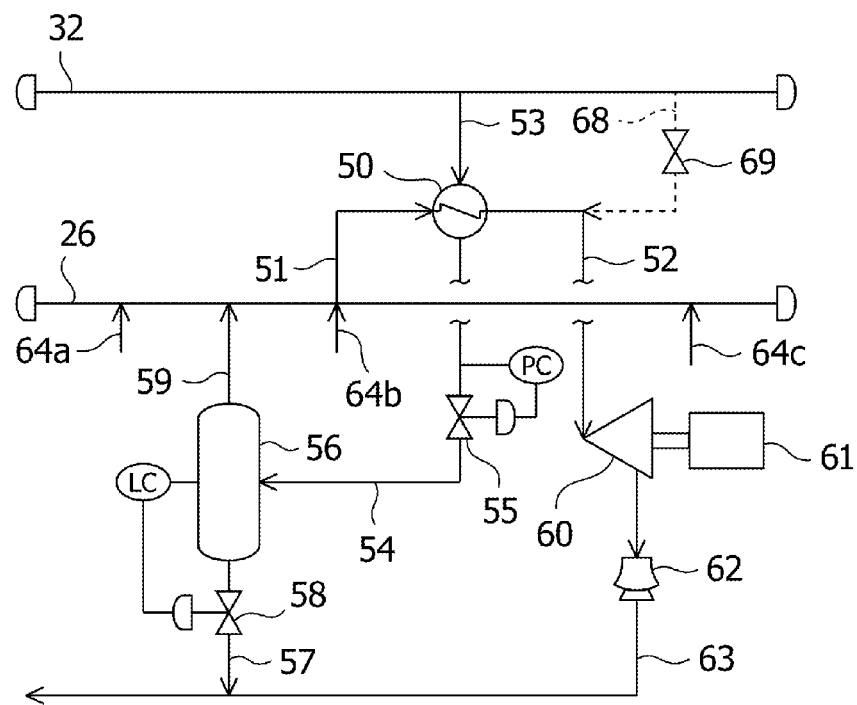
FIG. 2 is a schematic diagram showing an embodiment of the system for producing gasoline and generating power according to the present invention, which illustrates a flow of steam used for generating power.

Embodiments of the present invention will be described below with reference to the attached drawings. As shown in FIGS. 1 and 2, a gasoline production and power generation system according to the present embodiment includes main components such as a steam reformer 10, which is configured to generate reformed gas by steam-reforming hydrocarbon gas such as natural gas, a methanol synthesis column 30, which is configured to synthesize methanol from the reformed gas generated by the steam reformer, a gasoline synthesis column 40, which is configured to synthesize gasoline from the methanol synthesized by the methanol synthesis column, a low-pressure steam heat exchanger 25, which is arranged between the steam reformer and the methanol synthesis column and configured to obtain low-pressure steam from the reformed gas, a superheater 50, which is configured to superheat the low-pressure steam obtained by the heat exchanger, and a low-pressure steam turbine 60, which is configured to generate power by using the steam superheated by the superheater.

The steam reformer 10 is provided with main components such as a reaction tube 11 for steam reforming, a burning portion (not shown) 12 disposed around the reaction tube 11, a waste heat recovery portion 12, which is configured to recover waste heat of flue gas generated in the burning portion, and a stack 13, which is configured to release the flue gas to the atmosphere after waste heat has been recovered therefrom. The reaction tube 11, which includes a steam reforming catalyst charged inside the tube, is a device for generating hydrogen, carbon monoxide, and carbon dioxide from natural gas containing methane as its main ingredient by carrying out the following reactions. For the steam reforming catalyst, known catalysts such as a nickel-based catalyst can be used, for example.

$$CH_4 + H_2O \rightarrow 3H_2 + CO \quad (1)$$

$$CO + H_2O \rightarrow H_2 + CO_2 \quad (2)$$

To a side of an inlet port of the reaction tube 11 of the steam reformer 10, a feedstock supply line 14 for supplying natural gas which is a feedstock and a steam supply line 15 for supplying steam from a boiler and the like (not shown) are connected. To a side of an outlet port of the reaction tube 11, a reformed gas supply line 21 is connected, which is a line for supplying reformed gas containing hydrogen, carbon monoxide, and carbon dioxide generated by a steam-reforming reaction as its main ingredients to the methanol synthesis column 30. Also connected to the steam reformer 10 is a fuel supply line 16 for supplying a fuel to the burning portion (not shown) for heating the reaction tube 11.

The reformed gas supply line 21 is provided with a high-pressure steam heat exchanger 23 configured to obtain high-pressure steam from the reformed gas in the line, the low-pressure steam heat exchanger 25 configured to obtain low-pressure steam from the reformed gas in the line, and a compressor 22 configured to compress the reformed gas that has gone through the heat exchangers to obtain a pressure suitable for the synthesis of methanol, which are arranged in this order from the side of the steam reformer 10. The heat exchangers 23, 25 for high-pressure steam and low-pressure steam generate steam by performing heat exchange with the reformed gas. The compressor 22 compresses the reformed gas with a temperature lowered by the heat exchangers to a predetermined pressure before supplying the same to the methanol synthesis column 30.

The high-pressure steam heat exchanger 23 is provided with a high-pressure steam line 24 for supplying the generated high-pressure steam to a facility for a predetermined purpose. The low-pressure steam heat exchanger 25 is provided with a low-pressure steam line 26 for supplying the generated low-pressure steam to the low-pressure steam turbine 60 illustrated in FIG. 2.

The methanol synthesis column 30 is a device configured to synthesize methanol from reformed gas by running the following reactions.

$$CO + 2H_2 \rightarrow CH_3OH \quad (3)$$

$$CO_2 + 3H_2 \rightarrow CH_3OH + H_2O \quad (4)$$

The methanol synthesis column 30 includes a methanol synthesis catalyst charged inside the tube. For the methanol synthesis catalyst, known catalysts such as a copper-based catalyst can be used. A methanol supply line 31 is connected to methanol synthesis column 30, which is a line for supplying methanol synthesized by the methanol synthesis column 30 to the gasoline synthesis column 40. In addition to the synthesized methanol, liquid crude methanol containing water, which is a byproduct of the reaction of Formula (4), flows in the methanol supply line 31.

The methanol synthesis reaction run in the methanol synthesis column 30 is an exothermic reaction. Accordingly, middle-pressure steam can be obtained from water by using thermal energy generated by the methanol synthesis reaction run in the methanol synthesis column 30 as a heat source. The methanol synthesis column 30 is provided with a middle-pressure steam line 32 for supplying the middle-pressure steam that has been obtained in the above-described manner to a facility for a predetermined purpose, such as the superheater 50.

The gasoline synthesis column 30 is a device configured to synthesize gasoline from methanol by running the reactions expressed by the following Formulae.

$$2CH_3OH \rightarrow CH_3OCH_3 + H_2O \quad (5)$$

$$\frac{1}{2}nCH_3OCH_3 \rightarrow (CH_2)n + \frac{1}{2}nH_2O \quad (6)$$

As described above, methanol is synthesized by the gasoline synthesis reaction expressed by Formula (6) into gasoline via the dimethyl ether (DME) synthesis reaction expressed by Formula (5). In the gasoline synthesis column 40, two types of catalysts including a DME synthesis catalyst and a gasoline synthesis catalyst are provided in two stages so that the two reactions can be run in stages. For the DME synthesis catalyst, known catalysts such as an aluminosilicate type zeolite-based catalyst can be used, for example. In addition, for the gasoline synthesis catalyst also, known catalysts such as an aluminosilicate type zeolite-based catalyst can be used.

A gasoline supply line 41 is connected to the gasoline synthesis column 40, which is a line for supplying gasoline synthesized by the gasoline synthesis column 40 to storage facilities (not shown). In addition, the above-described reaction run in the gasoline synthesis column 40 is an exothermic reaction. Accordingly, middle-pressure steam can be obtained from water by using thermal energy generated by the reaction run in the gasoline synthesis column 40 as a heat source. The gasoline synthesis column 40 is provided with a middle-pressure steam line 42 for supplying the middle-pressure steam obtained in the above-described manner to a facility for a predetermined purpose, such as the superheater 50.

As shown in FIG. 2, the superheater 50 is provided with a low-pressure steam extraction line 51 for supplying a part of low-pressure steam from the low-pressure steam line 26 to the superheater 50, a superheated steam supply line 52 for supplying the low-pressure steam superheated by the superheater 50 to the low-pressure steam turbine 60, a middle-pressure steam extraction line 53 for supplying a part of middle-pressure steam from the middle-pressure steam line 32 to the superheater 50 as a superheat source, and a waste steam line 54 in which the waste steam used by the superheater 50 flows. In other words, the superheater 50 is a heat exchanger which superheats the low-pressure steam generated by the low-pressure steam heat exchanger 25 and its heat source is the middle-pressure steam generated by the methanol synthesis column 30. Note that the heat source can be any middle-pressure steam, i.e., the steam generated by the methanol synthesis column 30, the steam generated by the gasoline synthesis column 40, or both.

The low-pressure steam turbine 60 is provided with a generator 61, which is driven by the turbine and configured to generate power, and a steam condenser 62, which is configured to condense the steam used for driving the turbine back into water. A discharge line 63 is connected to the steam condenser 62, which is a line for discharging a steam condensate into the steam generation system to be recycled there.

The waste steam line 54 is provided with a valve 55, which can be controlled to be opened or closed according to the steam pressure in the line. The waste steam line 54 is connected to a gas-liquid separation device 56. The gas-liquid separation device 56 is a device configured to perform gas-liquid separation for separating steam that has been introduced therein into reusable steam and condensed water. The gas-liquid separation device 56 is provided with a steam return line 59 for returning the reusable steam to the low-pressure steam line 26 and a condensed water line 57 for discharging the condensed water into a condensed water line 63. The low-pressure steam line 26 can be provided with an auxiliary line for supplying steam generated in a waste heat recovery boiler (not shown) to the low-pressure steam line where necessary. The condensed water line 57 is provided with a valve 58 that can be controlled to be opened or closed in accordance with the liquid level of the condensed water in the gas-liquid separation device 56.

In the above-described configuration, first, natural gas and steam from the boiler (not shown) are respectively supplied to the reaction tube 11 of the steam reformer 10 via the feedstock supply line 14 and the steam supply line 15. In order to suppress precipitation of carbon on the catalyst in the reaction tube, it is preferable that the steam be supplied at a molar ratio of 2 or higher compared with hydrogen contained in the natural gas.

The fuel is supplied to the burning portion (not shown) of the steam reformer 10 via the fuel supply line 16. The fuel is burned in the burning portion together with air to heat the reaction tube 11 up to a temperature of about 800 to 900° C. The temperature of the flue gas containing carbon dioxide generated in the burning portion is about 1,000° C., and after having gone through heat recovery in the waste heat recovery portion 12, the flue gas is released from the stack 13 into the atmosphere.

On the other hand, the natural gas and the steam that have been supplied to the reaction tube 11 are converted by the steam-reforming reaction into reformed gas run in the reaction tube 11. The temperature of the reformed gas is about 800 to 900° C., and the reformed gas is first introduced into the high-pressure steam heat exchanger 23 via a reformed gas supply line 18. In the high-pressure steam heat exchanger 23, boiler water and the like are heated with the reformed gas, thus high-pressure steam having the temperature of about 200° C. or higher, for example, and a corresponding saturated steam pressure is generated, and thereby heat is recovered from the reformed gas. The high-pressure steam is supplied to a facility of a predetermined purpose via the high-pressure steam line 24.

The temperature of the reformed gas is lowered by the heat recovery performed by the high-pressure steam heat exchanger 23 to a temperature of about 200 to 300° C., for example, before being introduced into the low-pressure steam heat exchanger 25. In the low-pressure steam heat exchanger 25, the reformed gas heats the boiler water and the like, thus generates low-pressure steam having a temperature of about 100 to 180° C., preferably a temperature of about 100 to 180° C., for example, and a corresponding saturated steam pressure, and thereby heat is recovered from the reformed gas. The reformed gas cooled by the heat recovery down to the temperature of about 100 to 180° C. is further cooled with cooling water and an air cooler before being introduced into the compressor 22. In the compressor 22, the temperature of the reformed gas is controlled to a temperature suitable for a methanol synthesis reaction (e.g., about 200° C.) before supplying the reformed gas to the methanol synthesis column 30.

In the methanol synthesis column 30, methanol is synthesized by the reactions expressed by Formulae (3) and (4) from the reformed gas and carbon dioxide gas. Because the methanol synthesis reaction is an exothermic reaction, middle-pressure steam with a temperature of about 250° C. and a corresponding saturated steam pressure can be generated in the methanol synthesis column 30 due to thermic energy. The methanol synthesized by the methanol synthesis column 30 is supplied to the gasoline synthesis column 40 via the methanol supply line 31 as crude methanol containing water. The middle-pressure steam is supplied to a facility of a predetermined purpose via the middle-pressure steam line 32.

In the gasoline synthesis column 40, gasoline is synthesized from methanol by running the reactions of Formulae (5) and (6). Because the gasoline synthesis reaction is also an exothermic reaction, middle-pressure steam with a temperature of about 250° C. and a corresponding saturated steam pressure can be generated in the gasoline synthesis column 40 due to thermic energy. The gasoline synthesized by the gasoline synthesis column 40 is supplied to the storage facilities (not shown) via the gasoline supply line 41. The middle-pressure steam is supplied to a facility of a predetermined purpose via the middle-pressure steam line 42.

Next, a part of the low-pressure steam which flows through the low-pressure steam line 26 is introduced into the superheater 50 via the low-pressure steam extraction line 51 as illustrated in FIG. 2. In addition, a part of the middle-pressure steam which flows through the middle-pressure steam line 32 is introduced to the superheater 50 via the middle-pressure steam extraction line 53 to superheat the low-pressure steam. By performing the superheating, the temperature of the low-pressure steam can be raised to a temperature higher than the temperature of the saturated steam by about 50 to 100° C. The low-pressure steam that has been superheated in the above-described manner is supplied to the low-pressure steam turbine 60 via the superheated steam supply line 52. In the low-pressure steam turbine 60, the superheated low-pressure steam is inflated, the turbine is driven by the kinetic energy of the inflated steam, and thereby the generator 61 generates power.

Because the low-pressure steam supplied to the low-pressure steam turbine 60 has been superheated as described above, the level of wetness on the side of the outlet port of the low-pressure steam turbine can be reduced, thus the superheated low-pressure steam can be inflated to have a steam pressure of a low degree of vacuum, a high specific enthalpy can be obtained, and thereby the output from the low-pressure steam turbine 60 can be greatly improved. The steam that has been used by the low-pressure steam turbine 60 is condensed by the steam condenser 62 before being recycled into the steam generation system via the condensed water line.

On the other hand, the middle-pressure steam that has been used by the superheater 50 is supplied to the gas-liquid separation device 56 via the waste steam line 54. In the gas-liquid separation device 56, the pressure of the middle-pressure steam of which the temperature has been lowered due to the use thereof for the superheating is lowered to the same pressure as that of the low-pressure steam, and then is gas-liquid separated into reusable steam and condensed water. The condensed water is discharged into the condensed water line via the condensed water line 57. The steam is supplied to the low-pressure steam line 26 via the steam return line 59, then is superheated by the superheater 50, and the superheated steam can be reused for power generation by the low-pressure steam turbine 60.

Alternatively, instead of using the superheater 50, the low-pressure steam can be superheated by providing and using a steam mixing line 68 to the middle-pressure steam line 32 as illustrated in FIG. 2. The steam mixing line 68 is a line for mixing a part of the middle-pressure steam that flows through the middle-pressure steam line with the low-pressure steam that flows through the low-pressure steam extraction line 51. With the above-described configuration, the temperature of the low-pressure steam can be raised to a temperature higher than the temperature of the saturated steam by about 50 to 100° C. The configuration that uses the steam mixing line 68 may of course be used together with the superheater 50. By providing the steam mixing line 68 with an open-close valve 69, superheating means can be selected between the heat exchange by the superheater 50 and the mixing by the steam mixing line 68.

Although FIG. 1 illustrates the gasoline synthesis column 40, a DME synthesis column configured to produce DME by performing the process only up to a stage of the DME synthesis reaction expressed by Formula (5) can be provided instead of the gasoline synthesis column 40. Because the DME synthesis reaction also is an exothermic reaction, the middle-pressure steam can be generated by the DME synthesis column. Further alternatively, if a synthesis column that performs the Fischer-Tropsch process is provided instead of the methanol synthesis column 30 and the gasoline synthesis column 40 illustrated in FIG. 1, a diesel fuel can be obtained from the reformed gas. Because a Fischer-Tropsch synthesis reaction also is an exothermic reaction, the middle-pressure steam can also be generated in this configuration.

Figure 3:
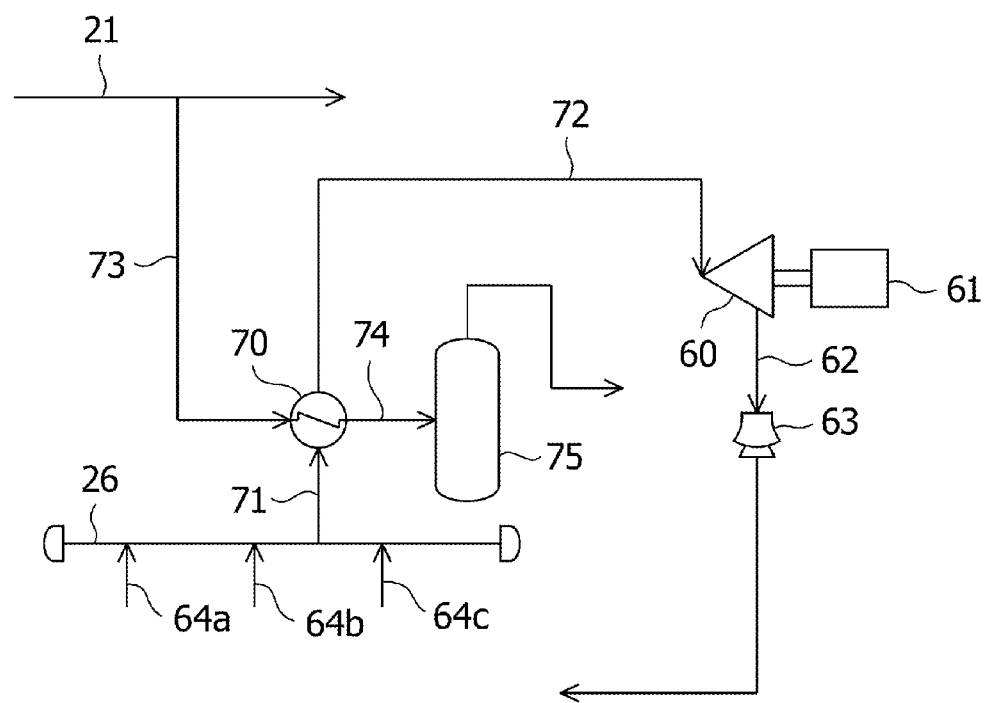
FIG. 3 is a schematic diagram showing another embodiment of the system for producing gasoline and generating power according to the present invention, which illustrates a flow of steam used for generating power.
Figure 4:
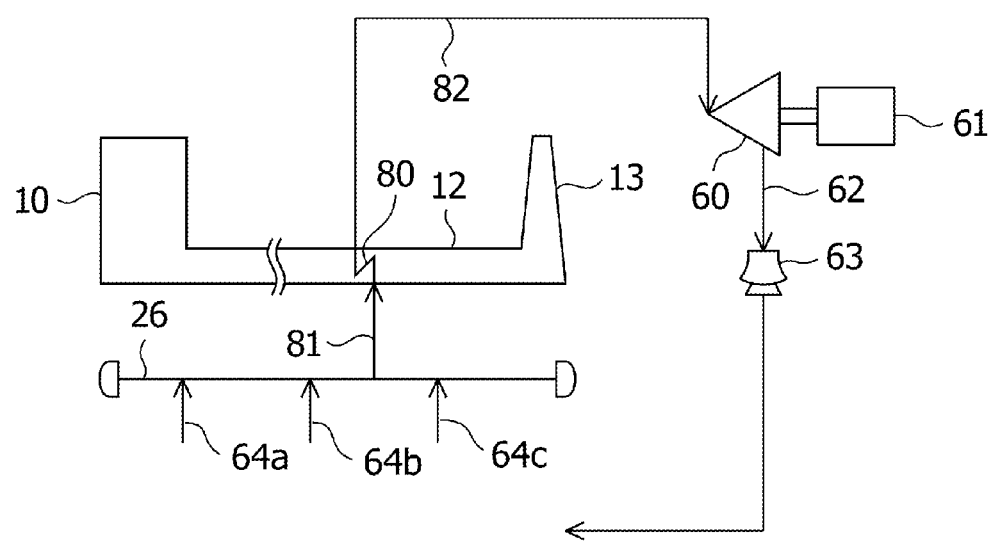
FIG. 4 is a schematic diagram showing yet another embodiment of the system for producing gasoline and generating power according to the present invention, which illustrates a flow of steam used for generating power.

In the present invention, the heat source for superheating the low-pressure steam is not limited to the heat from the middle-pressure steam generated in the methanol synthesis column and the gasoline synthesis column. For example, alternatively, heat from the reformed gas generated by the steam reformer and heat from the flue gas can be used as the heat source. As configurations that can be used alternatively to the configuration illustrated in FIG. 2, FIG. 3 illustrates a configuration that uses the reformed gas generated by the steam reformer and FIG. 4 illustrates a configuration that uses flue gas from the steam reformer. In FIGS. 3 and 4, the same components as those illustrated in FIG. 2 are provided with the same reference signs and detailed descriptions thereof will not be repeated below.

As shown in FIG. 3, in the configuration in which the reformed gas generated by the steam reformer is used as the heat source for superheating, a superheater 70 is provided with a low-pressure steam extraction line 71 for supplying a part of the low-pressure steam from the low-pressure steam line 26 to the superheater 70, a superheated steam supply line 72 for supplying the low-pressure steam superheated by the superheater 70 to the low-pressure steam turbine 60, a reformed gas extraction line 73 for supplying a part of the reformed gas from the reformed gas supply line 21 to the superheater 70 as the superheat source, and a reformed gas discharge line 74 in which the reformed gas that has been used by the superheater 70 flows. For the position of connection of the reformed gas extraction line 73 with the reformed gas supply line 21, the reformed gas extraction line 73 can be connected at a location between the steam reformer 10 and the high-pressure steam heat exchanger 23 or a location between the high-pressure steam heat exchanger 23 and the low-pressure steam heat exchanger 25 illustrated in FIG. 1. The reformed gas discharge line 74 is connected to the compressor 22 illustrated in FIG. 1. In addition, the reformed gas discharge line 74 is provided with a gas-liquid separation device 75, which is configured to remove condensed water from the reformed gas that has been used for the superheating.

In the above-described configuration, a part of the low-pressure steam which flows through the low-pressure steam line 26 is introduced into the superheater 70 via the low-pressure steam extraction line 71. In addition, a part of the reformed gas which flows through the reformed gas supply line 21 is introduced to the superheater 70 via the reformed gas extraction line 73 to superheat the low-pressure steam. By performing the superheating, the temperature of the low-pressure steam can be raised to a temperature higher than the temperature of the saturated steam by about 50 to 150° C., for example. The low-pressure steam that has been superheated in the above-described manner is supplied to the low-pressure steam turbine 60 via the superheated steam supply line 72. In the low-pressure steam turbine 60, the turbine is driven as described above and thereby power is generated by the generator 61. In this configuration also, the output from the low-pressure steam turbine 60 can be greatly improved and the level of wetness of the steam that has been used by the low-pressure steam turbine 60 on the side of the outlet port of the turbine can be improved.

On the other hand, the reformed gas that has been used by the superheater 70 is introduced into the gas-liquid separation device 75 via the reformed gas discharge line 74. Condensed water is separated by the gas-liquid separation device 75, then the condensed water is supplied to the methanol synthesis column 30 via the compressor 22 illustrated in FIG. 1 as the feedstock for the methanol synthesis reaction.

As shown in FIG. 4, in the configuration in which the flue gas from the steam reformer is used as the heat source of the superheating, a superheater 80 is provided to the waste heat recovery portion 12 of the steam reformer 10. The superheater 80 is provided with a low-pressure steam extraction line 81 for supplying a part of the low-pressure steam from the low-pressure steam line 26 to the superheater 80 and a superheated steam supply line 82 for supplying the low-pressure steam that has been superheated by the superheater 80 to the low-pressure steam turbine 60.

In the above-described configuration, a part of the low-pressure steam which flows through the low-pressure steam line 26 is introduced into the superheater 80 via the low-pressure steam extraction line 81. The low-pressure steam is superheated by the flue gas that flows through the waste heat recovery portion 12 of the steam reformer 10. By performing this superheating, the temperature of the low-pressure steam can be raised to a temperature higher than the temperature of the saturated steam by about 50 to 150° C., for example. The low-pressure steam that has been superheated in the above-described manner is supplied to the low-pressure steam turbine 60 via the superheated steam supply line 82. In the low-pressure steam turbine 60, the turbine is driven as described above and thereby power is generated by the generator 61. In this configuration also, the output from the low-pressure steam turbine 60 can be greatly improved and the level of wetness of the steam that has been used by the low-pressure steam turbine 60 can be improved.

EXAMPLES

Simulations of the steam to be supplied to the steam turbine which can be obtained by the superheating were carried out for the embodiments illustrated in FIGS. 2 to 4. The results of the simulations are illustrated in Table 1. Conditions for the low-pressure steam to be the subject of the superheating in each embodiment were as follows:
  temperature: 143° C.,
  pressure: 3 kg/cm$^2$G, and
  flow rate: 114.3 t/h.

TABLE 1

|  | FIG. 2 | FIG. 3 | FIG. 4 |
| --- | --- | --- | --- |
| Temperature of superheat source (° C.) | 331 | 200 | 300 |
| Pressure of superheat source (kg/cm$^2$G) | 26.5 | 18.0 | atmospheric pressure |
| Flow rate of superheat source (t/h) | 7.84 | 63.5 | 100 |
| Temperature of superheated steam (° C.) | 210 | 190 | 210 |
| Pressure of superheated steam (kg/cm$^2$G) | 2.8 | 2.8 | 2.8 |
| Temperature of superheat source after being used for superheating (° C.) | 223 | 155 | 220 |
| Thermal energy for superheating (kcal/h) | 3.96 × 10$^6$ | 2.8 × 10$^6$ | 3.96 × 10$^6$ |

According to FIGS. 2 and 4, the steam with the temperature of 210° C. and the pressure of 3 kg/cm$^2$G is obtained by the superheating. If this steam is to be used for turbine-driven power generation, the amount of heat of 95 kcal/kg is obtained by subtracting 590 kcal/kg from 685 kcal/kg, and as a result, the turbine output is 12,620 kw. On the other hand, if the saturated steam with the pressure of 3 kg/cm$^2$G is to be used for turbine-driven power generation, the amount of heat of 47 kcal/kg is obtained by subtracting 608 kcal/kg from 655 kcal/kg, and as a result, the turbine output is 6,240 kw. Accordingly, by carrying out the superheating as illustrated in FIGS. 2 and 4, the turbine output can be nearly doubled.

In addition, the moisture content is usually distilled off from methanol generated by a methanol synthesis column. In the reaction for synthesizing gasoline from methanol, water is generated at the same time as gasoline as expressed by Formulae (5) and (6). Accordingly, in the configuration illustrated in FIG. 1, provision of a distillation column between the methanol synthesis column and the gasoline synthesis column can be omitted. In a plant which includes a steam reformer and a methanol synthesis column and produces 2,500 tons of methanol per day, the thermal amount of about 60×10$^6$ kcal is required for the distillation, and in a configuration in which the distillation column is omitted, saturated steam with the pressure of 3 kg/cm$^2$G can be generated by the heat exchanger for the reformed gas of the steam reformer at the flow rate of 114 t/h.

DESCRIPTION OF REFERENCE NUMERALS

10: Steam reformer
11: Reaction tube
12: Waste heat recovery portion
13: Stack
14: Feedstock supply line
15: Steam supply line
16: Fuel supply line
21: Reformed gas supply line
22: Compressor
23: High-pressure steam heat exchanger
24: High-pressure steam line
25: Low-pressure steam heat exchanger
26: Low-pressure steam line
30: Methanol synthesis column
31: Methanol supply line
32: Middle-pressure steam line
40: Gasoline synthesis column
41: Gasoline supply line
42: Middle-pressure steam line
50, 70, 80: Superheaters
51, 71, 81: Low-pressure steam extraction lines
52, 72, 82: Superheated steam supply lines
53: Middle-pressure steam extraction line
54: Waste steam line
55: Valve
56: Gas-liquid separation device
57: Condensed water line
58: Valve
59: Steam return line
60: Low-pressure steam turbine
61: Generator
62: Steam condenser
63: Condensed water line
73: Reformed gas extraction line
74: Reformed gas discharge line
75: Gas-liquid separation device

The invention claimed is:

1. A system for producing a liquid fuel from hydrocarbon gas and for generating power, the system comprising:
  a steam-reforming device configured to generate reformed gas by performing a steam-reforming reaction with hydrocarbon gas;
  a synthesis column configured to synthesize gasoline, dimethyl ether, or a diesel fuel from the reformed gas via methanol;
  a heat exchanging device configured to obtain saturated steam with a temperature of 180° C. or lower by performing heat exchange with the reformed gas before the reformed gas is used by the synthesis column;

a superheating device configured to superheat the saturated steam by using a heat source with a temperature of 200° C. or higher generated within the system and obtain superheated steam; and a power generation device configured to generate power by using the superheated steam, wherein the superheating device uses steam generated by an exothermic reaction run in the synthesis column as a heat source.

2. The system according to claim 1, wherein a part of the reformed gas obtained by the steam-reforming device is used as the heat source for the superheating device.

3. The system according to claim 1, wherein flue gas generated by from a burning portion of the steam-reforming device is used as the heat source for the superheating device.

* * * * *